United States Patent
Kurth et al.

(10) Patent No.: US 7,963,947 B2
(45) Date of Patent: Jun. 21, 2011

(54) APPARATUS, SYSTEM, AND METHOD OF SHIELDING THE SHARP TIP OF A TRANSSEPTAL GUIDEWIRE

(75) Inventors: Paul Kurth, Santa Barbara, CA (US); Andrew W. Armour, Swarthmore, PA (US)

(73) Assignee: Pressure Products Medical Supplies, Inc., San Pedro, CA (US)

( * ) Notice: Subject to any disclaimer, the term of this patent is extended or adjusted under 35 U.S.C. 154(b) by 72 days.

(21) Appl. No.: 12/015,097

(22) Filed: Jan. 16, 2008

(65) Prior Publication Data
US 2009/0182281 A1   Jul. 16, 2009

(51) Int. Cl.
*A61M 5/178* (2006.01)
(52) U.S. Cl. .................................. 604/164.08; 604/159
(58) Field of Classification Search ............. 604/164.08, 604/159
See application file for complete search history.

(56) References Cited

U.S. PATENT DOCUMENTS

| | | | |
|---|---|---|---|
| 3,561,445 A * | 2/1971 | Katerndahl et al. .......... | 604/159 |
| 3,995,628 A * | 12/1976 | Gula et al. ................. | 604/159 |
| 4,676,249 A | 6/1987 | Arenas et al. | |
| 4,724,846 A | 2/1988 | Evans, III | |
| 5,120,308 A | 6/1992 | Hess | |
| 5,125,905 A | 6/1992 | Wright et al. | |
| 5,190,528 A | 3/1993 | Fonger et al. | |
| 5,273,042 A | 12/1993 | Lynch et al. | |
| 5,279,573 A | 1/1994 | Klosterman | |
| 5,282,479 A | 2/1994 | Havran | |
| 5,312,341 A | 5/1994 | Turi | |
| 5,366,444 A | 11/1994 | Martin | |
| 5,370,609 A | 12/1994 | Drasler et al. | |
| 5,403,338 A | 4/1995 | Milo | |
| 5,438,993 A | 8/1995 | Lynch et al. | |
| 5,454,785 A | 10/1995 | Smith | |

(Continued)

FOREIGN PATENT DOCUMENTS

CA   2212657   3/1998

(Continued)

OTHER PUBLICATIONS

International Search Report dated Jan. 22, 2009, application No. PCT/US2008/080123.

(Continued)

*Primary Examiner* — Nicholas D Lucchesi
*Assistant Examiner* — Rebecca E Eisenberg
(74) *Attorney, Agent, or Firm* — RatnerPrestia (57) ABSTRACT

Apparatus, system, and methods for introducing a sharp tip of a transseptal guidewire through a hub of a transseptal needle and into a lumen of a transseptal needle are provided. The apparatus includes a holder that contains the transseptal guidewire and a shield coupled to the holder. The shield has a wall defining a lumen that accommodates the sharp tip of the transseptal guidewire. The cross-sectional shape of the wall is substantially constant along at least a portion of its length and sized to fit within the lumen of the transseptal needle, thereby inhibiting contact between the sharp tip of the transseptal guidewire and the hub of the transseptal needle when the wall of the shield is positioned to extend into the lumen of the transseptal needle. The lumen of the shield has a substantially constant cross-sectional area along at least a portion of its length and an outer surface of the wall of the shield is cylindrical along the same length.

26 Claims, 4 Drawing Sheets

U.S. PATENT DOCUMENTS

| | | | |
|---|---|---|---|
| 5,484,419 A | 1/1996 | Fleck | |
| 5,507,300 A | 4/1996 | Mukai et al. | |
| 5,730,150 A | 3/1998 | Peppel et al. | |
| 5,785,675 A | 7/1998 | Drasler et al. | |
| 5,810,835 A * | 9/1998 | Ryan et al. | 606/108 |
| 5,827,202 A | 10/1998 | Miraki et al. | |
| 5,871,495 A | 2/1999 | Mueller | |
| 5,895,404 A | 4/1999 | Ruiz | |
| 5,968,059 A | 10/1999 | Ellis et al. | |
| 5,976,164 A | 11/1999 | Bencini et al. | |
| 5,989,278 A | 11/1999 | Mueller | |
| 6,002,955 A | 12/1999 | Willems et al. | |
| 6,011,988 A | 1/2000 | Lynch et al. | |
| 6,045,565 A | 4/2000 | Ellis et al. | |
| 6,059,484 A | 5/2000 | Greive | |
| 6,063,082 A | 5/2000 | DeVore et al. | |
| 6,093,185 A | 7/2000 | Ellis et al. | |
| 6,096,001 A | 8/2000 | Drasler et al. | |
| 6,123,084 A | 9/2000 | Jandak et al. | |
| 6,129,697 A | 10/2000 | Drasler et al. | |
| 6,216,573 B1 | 4/2001 | Moutafis et al. | |
| 6,231,564 B1 | 5/2001 | Gambale | |
| 6,238,406 B1 | 5/2001 | Ellis et al. | |
| 6,258,061 B1 | 7/2001 | Drasler et al. | |
| 6,290,709 B1 | 9/2001 | Ellis et al. | |
| 6,402,740 B1 | 6/2002 | Ellis et al. | |
| 6,416,490 B1 | 7/2002 | Ellis et al. | |
| 6,423,027 B1 | 7/2002 | Gonon | |
| 6,423,028 B1 | 7/2002 | Gonon | |
| 6,451,017 B1 | 9/2002 | Moutafis et al. | |
| 6,471,683 B2 | 10/2002 | Drasler et al. | |
| 6,477,402 B1 | 11/2002 | Lynch et al. | |
| 6,511,493 B1 | 1/2003 | Moutafis et al. | |
| 6,537,266 B1 | 3/2003 | Mottola et al. | |
| 6,544,209 B1 | 4/2003 | Drasler et al. | |
| 6,551,281 B1 | 4/2003 | Raulerson et al. | |
| 6,558,366 B1 | 5/2003 | Drasler et al. | |
| 6,650,923 B1 | 11/2003 | Lesh et al. | |
| 6,660,003 B1 | 12/2003 | DeVore et al. | |
| 6,669,710 B2 | 12/2003 | Moutafis et al. | |
| 6,676,627 B1 | 1/2004 | Bonnette et al. | |
| 6,676,637 B1 | 1/2004 | Bonnette et al. | |
| 6,689,089 B1 | 2/2004 | Tiedtke et al. | |
| 6,692,456 B1 | 2/2004 | Eppstein et al. | |
| 6,719,718 B2 | 4/2004 | Bonnette et al. | |
| 6,749,617 B1 | 6/2004 | Palasis et al. | |
| 6,755,803 B1 | 6/2004 | Le et al. | |
| 6,764,483 B1 | 7/2004 | Bonnette et al. | |
| 6,805,684 B2 | 10/2004 | Bonnette et al. | |
| 6,808,508 B1 | 10/2004 | Zafirelis et al. | |
| 6,875,193 B1 | 4/2005 | Weisel et al. | |
| 6,890,353 B2 | 5/2005 | Cohn et al. | |
| 6,899,712 B2 | 5/2005 | Moutafis et al. | |
| 6,913,605 B2 | 7/2005 | Fletcher et al. | |
| 6,926,726 B2 | 8/2005 | Drasler et al. | |
| 6,945,951 B1 | 9/2005 | Bonnette et al. | |
| 6,953,466 B2 | 10/2005 | Palasis et al. | |
| 6,984,239 B1 | 1/2006 | Drasler et al. | |
| 7,048,733 B2 | 5/2006 | Hartley et al. | |
| 7,056,294 B2 | 6/2006 | Khairkhahan et al. | |
| 7,083,588 B1 | 8/2006 | Shmulewitz et al. | |
| 7,112,197 B2 | 9/2006 | Hartley et al. | |
| 2001/0001124 A1 | 5/2001 | Mueller | |
| 2001/0051785 A1 | 12/2001 | Bonnette et al. | |
| 2001/0051811 A1 | 12/2001 | Bonnette et al. | |
| 2001/0056257 A1 | 12/2001 | Drasler et al. | |
| 2002/0050197 A1 | 5/2002 | Moutafis et al. | |
| 2002/0062091 A1 | 5/2002 | Jacobsen et al. | |
| 2002/0143289 A1 | 10/2002 | Ellis et al. | |
| 2002/0169377 A1 | 11/2002 | Khairkhahan et al. | |
| 2002/0198550 A1 | 12/2002 | Nash et al. | |
| 2003/0009166 A1 | 1/2003 | Moutafis et al. | |
| 2003/0036712 A1 | 2/2003 | Heh et al. | |
| 2003/0040763 A1 | 2/2003 | Moutafis et al. | |
| 2003/0125660 A1 | 7/2003 | Moutafis et al. | |
| 2003/0144657 A1 | 7/2003 | Bowe et al. | |
| 2003/0171735 A1 | 9/2003 | Parker et al. | 604/507 |
| 2004/0015138 A1 | 1/2004 | Currier et al. | |
| 2004/0039342 A1 | 2/2004 | Eppstein et al. | |
| 2004/0049149 A1 | 3/2004 | Drasler et al. | |
| 2004/0073141 A1 | 4/2004 | Hartley et al. | |
| 2004/0092973 A1 | 5/2004 | Chanduszko et al. | |
| 2004/0122416 A1 | 6/2004 | Schweikert et al. | |
| 2004/0143262 A1 | 7/2004 | Visram et al. | |
| 2004/0153109 A1 | 8/2004 | Tiedtke et al. | |
| 2004/0193046 A1 | 9/2004 | Nash et al. | |
| 2004/0204672 A1 | 10/2004 | Palasis et al. | |
| 2004/0206365 A1 | 10/2004 | Knowlton | |
| 2004/0210194 A1 | 10/2004 | Bonnette et al. | |
| 2004/0210214 A1 | 10/2004 | Knowlton | |
| 2004/0210239 A1 | 10/2004 | Nash et al. | |
| 2004/0230211 A1 | 11/2004 | Moutafis et al. | |
| 2004/0267163 A1 | 12/2004 | Opie et al. | |
| 2005/0033334 A1 | 2/2005 | Santra et al. | |
| 2005/0065507 A1 | 3/2005 | Hartley et al. | |
| 2005/0101984 A1 | 5/2005 | Chanduszko et al. | |
| 2005/0149097 A1 | 7/2005 | Regnell et al. | |
| 2005/0159738 A1 | 7/2005 | Visram et al. | |
| 2005/0222557 A1 | 10/2005 | Baxter et al. | |
| 2005/0222558 A1 | 10/2005 | Baxter et al. | |
| 2005/0228468 A1 | 10/2005 | Macoviak et al. | |
| 2005/0234436 A1 | 10/2005 | Baxter et al. | |
| 2005/0245847 A1 | 11/2005 | Schaeffer | |
| 2005/0251105 A1 | 11/2005 | Peyman | |
| 2005/0256450 A1 | 11/2005 | Palasis et al. | |
| 2005/0283150 A1 | 12/2005 | Moutafis et al. | |
| 2006/0009715 A1 | 1/2006 | Khairkhahan et al. | |
| 2006/0009737 A1 | 1/2006 | Whiting et al. | |
| 2006/0047267 A1 | 3/2006 | Gately et al. | |
| 2006/0064062 A1 | 3/2006 | Gurusamy et al. | |
| 2006/0064123 A1 | 3/2006 | Bonnette et al. | |
| 2006/0074398 A1 | 4/2006 | Whiting et al. | |
| 2006/0079769 A1 | 4/2006 | Whiting et al. | |
| 2006/0079787 A1 | 4/2006 | Whiting et al. | |
| 2006/0079870 A1 | 4/2006 | Barry | |
| 2006/0095015 A1 | 5/2006 | Hobbs et al. | |
| 2006/0095052 A1 | 5/2006 | Chambers | |
| 2006/0122680 A1 | 6/2006 | Auth et al. | |
| 2006/0200113 A1 | 9/2006 | Haffner et al. | |
| 2006/0241648 A1 | 10/2006 | Bleich et al. | |
| 2007/0043307 A1 | 2/2007 | Raulerson et al. | |
| 2007/0185413 A1 | 8/2007 | Asai et al. | |
| 2007/0270741 A1 | 11/2007 | Hassett et al. | |

FOREIGN PATENT DOCUMENTS

| | | |
|---|---|---|
| CA | 2244596 | 2/1999 |
| CA | 2322452 | 9/1999 |
| CA | 2499753 | 4/2004 |
| DE | 9212575.1 | 11/1992 |
| EP | 0470781 | 2/1992 |
| EP | 0554754 A | 8/1993 |
| EP | 0 587 984 A1 | 3/1994 |
| EP | 829239 | 3/1998 |
| EP | 0 842673 A1 | 5/1998 |
| EP | 0873719 | 10/1998 |
| EP | 895752 | 2/1999 |
| EP | 1484025 | 12/2004 |
| EP | 1570878 A | 9/2005 |
| EP | 1602339 | 12/2005 |
| EP | 1 920795 A1 | 5/2008 |
| GB | 2263407 | 7/1993 |
| JP | 10225459 | 8/1998 |
| MX | PA02010065 | 3/2003 |
| WO | WO9324830 | 12/1993 |
| WO | WO9410917 | 5/1994 |
| WO | WO 97/47350 A | 12/1997 |
| WO | WO9839038 | 9/1998 |
| WO | WO9922655 | 5/1999 |
| WO | WO9933510 | 7/1999 |
| WO | WO9944523 | 9/1999 |
| WO | WO9944524 | 9/1999 |
| WO | WO0150966 | 7/2001 |
| WO | WO0178596 | 10/2001 |
| WO | WO 03/008005 | 1/2003 |
| WO | WO03045259 | 6/2003 |
| WO | WO03063942 | 8/2003 |
| WO | WO03077733 | 9/2003 |

| WO | WO2004026147 | 4/2004 |
| WO | WO2006/060019 | 6/2006 |
| WO | WO2006094222 | 9/2006 |
| WO | WO 2006/119503 A1 | 11/2006 |
| WO | WO2005/046487 | 5/2007 |

OTHER PUBLICATIONS

Emile G. Daoud, MD, "Hands on Transseptal Catheterization", pp. 212-214, Heart Rhythm, vol. 2, No. 2, Feb. 2005.

John Hummel, MD, FACC, Transseptal Catheterization With Intracardiac Echocardiography (ICE), pp. 1-6, Technology Focus, Published Oct. 12, 2004.

Takayuki Hirano, MD Makoto Komatsu, MEng, Toshiro Saeki, BSc, Hiroshi Uenohara, MD, Akira Takahashi, MD[4], Kazuyoshi Takayama, DEng, Takashi Yoshimoto, MD, "Enhancement of Fibinolytics With a Laser-Induced Liquid Jet", Medline, Jun. 11, 2001, Wiley-Liss.

Douek PC, Gandjbakche A, Leon MB, Bonner RF, "Functional Properties of a Prototype Rheolytic Catheter for Percutaneous Thrombectomy. In Vitro Investigations.", pp. 547-552, InvestRadiol, May 29, 1994.

International Search Report dated Apr. 3, 2009, application No. PCT/US2009/030703.

* cited by examiner

APPARATUS, SYSTEM, AND METHOD OF SHIELDING THE SHARP TIP OF A TRANSSEPTAL GUIDEWIRE

FIELD OF THE INVENTION

The present invention relates generally to surgical equipment. More particularly, the present invention relates to apparatus, systems, and methods for introducing the sharp tip of a transseptal guidewire into a lumen of a transseptal needle while inhibiting contact between the sharp tip of the transseptal guidewire and the hub of the transseptal needle.

BACKGROUND OF THE INVENTION

Guidewires are typically used to navigate catheters. For example, U.S. Patent Application Publication No. 2004/0073141 describes a guidewire that assists with endovascular deployment. The guidewire has a J curve and atruamatic tip to prevent damage to tissue. Introducers can be used to straighten the tips of such guidewires. For example, U.S. Pat. Nos. 5,125,905 and 5,282,479 relate to a guidewire straightener and protective tube to introduce a catheter into a patient's blood vessel.

Transseptal introducer systems are typically used to introduce Brockenbrough needles or other puncture devices into the heart of a patient to perforate the intra-atrial septum. For example, a transseptal guidewire is described in U.S. patent application Ser. No. 11/875,365, which is incorporated herein in its entirety by reference. The transseptal guidewire differs from conventional guidewires at least in that it has a tip that is sharp enough to puncture the septum, thereby providing a puncture device. Although the transseptal guidewire represents an improvement over prior puncture devices, damage to the sharp tip of the transseptal guidewire could render it unsuitable for use or require the surgeon to apply extra force to puncture the intra-atrial septum. For example, the sharp tip of the transseptal guidewire may be inadvertently damaged as it is introduced into the lumen of a transseptal needle through a hub of the needle or may be difficult to introduce into the lumen of the transseptal needle.

Accordingly, there remains a need for an apparatus, system and method for introducing the sharp tip of a transseptal guidewire into a lumen of a transseptal needle while inhibiting damage to the sharp tip of the transseptal guidewire.

SUMMARY OF THE INVENTION

In one aspect, the invention provides an apparatus for introducing a sharp tip of a transseptal guidewire through a hub of a transseptal needle and into a lumen of a transseptal needle while inhibiting damage to the sharp tip of the transseptal guidewire. The apparatus includes a holder configured to contain the transseptal guidewire and a shield coupled to the holder. The shield has a wall defining a lumen sized to accommodate the sharp tip of the transseptal guidewire. The cross-sectional shape of the wall is substantially constant along at least a portion of its length and is sized to fit within the lumen of the transseptal needle, thereby inhibiting contact between the sharp tip of the transseptal guidewire and the hub of the transseptal needle when the wall of the shield is positioned to extend into the lumen of the transseptal needle. The lumen of the shield has a substantially constant cross-sectional area along at least a portion of its length between proximal and distal ends of the shield, thereby facilitating insertion of the sharp tip of the transseptal guidewire through the lumen of the shield. An outer surface of the wall of the shield is cylindrical along at least a portion of its length between the proximal and distal ends of the shield, thereby facilitating insertion of the shield through the lumen of the transseptal needle to a point distal of the needle's hub and/or eliminating resistance between an outer surface of the shield and the inner surface of the lumen of the transseptal needle.

In another aspect, a system for perforating an intra-atrial septum is provided. The system includes a transseptal needle having proximal and distal ends, a hub positioned at the proximal end, and a lumen extending from the hub to the distal end. The system also includes a transseptal guidewire having a sharp tip sized to extend through the lumen of the transseptal needle. A holder at least partially contains the transseptal guidewire, and a shield is coupled to the holder. The shield has a wall defining a lumen sized to accommodate the sharp tip of the transseptal guidewire. The transseptal guidewire has a retracted position in which the sharp tip of the transseptal guidewire is contained within the lumen of the shield and an extended position in which the sharp tip of the transseptal guidewire extends distally from the shield and into the lumen of the transseptal needle. The shield has a first position in which the distal end of the shield does not extend into the lumen of the transseptal needle and a second position in which the distal end of the shield extends into the lumen of the transseptal needle to a position that is distal of the hub of the transseptal needle. The transseptal guidewire is in the retracted position when the shield is in the first position, and the transseptal guidewire is moved to the extended position when the shield is in the second position, thereby inhibiting contact between the sharp tip of the transseptal guidewire and the hub of the transseptal needle or the proximal end of the transseptal needle when the shield is in the second position.

According to yet another aspect, a method of shielding a sharp tip of a transseptal guidewire as it is introduced into a transseptal needle from a dispenser is provided. The method includes inserting a tip of a shield of the dispenser through a hub of the transseptal needle and into a lumen of the transseptal needle. The tip of the shield is then advanced to a point in the lumen distal of the hub without restriction. The sharp tip of the transseptal guidewire is introduced from a lumen of the shield of the dispenser and into the lumen of the transseptal needle at the point in the lumen distal of the hub, thereby avoiding contact between the sharp tip of the transseptal guidewire and the hub of the transseptal needle or a proximal end of the transseptal needle and associated damage to the sharp tip of the transseptal guidewire.

BRIEF DESCRIPTION OF THE DRAWINGS

The invention is best understood from the following detailed description when read in connection with the accompanying drawings, with like elements having the same reference numerals. This emphasizes that according to common practice, the various features of the drawings are not drawn to scale. On the contrary, the dimensions of the various features are arbitrarily expanded or reduced for clarity. Included in the drawings are the following figures.

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

Figure 1:
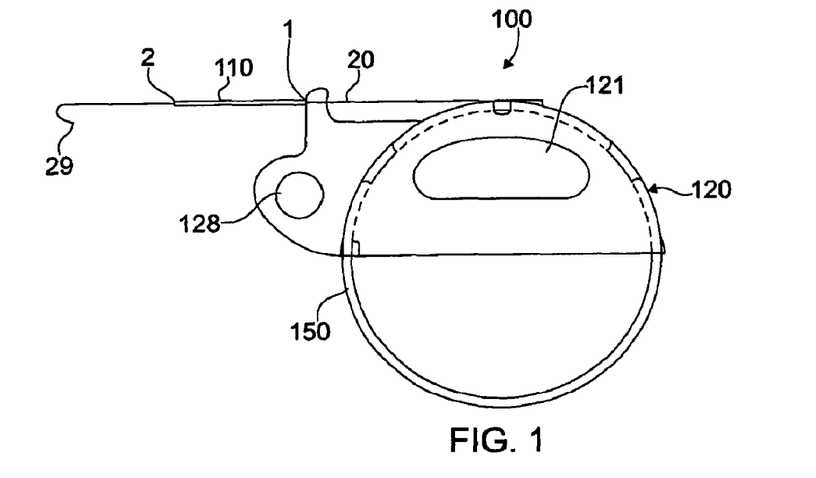
FIG. 1 is a plan view of a transseptal guidewire dispenser assembly according to an exemplary embodiment of the present invention.

Referring generally to the drawings (FIGS. 1-8B), in accordance with one exemplary embodiment, the invention provides a transseptal guidewire dispenser 100, shown assembled with a transseptal guidewire 20 in FIG. 1, for introducing a sharp tip 29 of the transseptal guidewire 20 through a hub 60 of a transseptal needle 80 and into a lumen 81 of the transseptal needle 80. The dispenser 100 includes a holder 150 that contains the transseptal guidewire 20 and a shield 110 coupled to the holder 150. Shield 110 has a wall 111 defining a lumen 115 that is sized to accommodate the sharp tip 29 of the transseptal guidewire 20. The cross-sectional shape of the wall 111 is substantially constant along at least a portion of its length and is sized to fit within the lumen 81 of the transseptal needle 80, thereby inhibiting contact between the sharp tip 29 of the transseptal guidewire 20 and the hub 60 of the transseptal needle 80 when the wall 111 of the shield 110 is positioned to extend into the lumen 81 of the transseptal needle 80. The lumen 115 of the shield 110 has a substantially constant cross-sectional area along at least a portion of its length between proximal 1 and distal 2 ends of shield 110, thereby facilitating insertion of the sharp tip 29 of the transseptal guidewire 20 through the lumen 115 of the shield 110. An outer surface of the wall of the shield 110 is substantially cylindrical along at least a portion of its length between the proximal 1 and distal ends 2 of the shield 110, thereby facilitating insertion of the shield 110 through the lumen 81 of the transseptal needle 80.

According to another aspect of the invention, an exemplary embodiment of a method for shielding a sharp tip 29 of a transseptal guidewire 20 as it is introduced into a transseptal needle 80 is provided. The tip 2 of the shield 110 is inserted through the hub 60 and into the lumen 81 of the transseptal needle 80. The tip 2 of the shield 110 is then advanced to a point in the lumen 81 distal of the hub 60 without restriction. The sharp tip 29 of the transseptal guidewire 20 is introduced from the lumen 115 of the shield 110 of the dispenser 100 and into the lumen 81 of the transseptal needle 80 at the point in the lumen 81 distal of the hub 60, thereby avoiding contact between the sharp tip 29 of the transseptal guidewire 20 and the hub 60 of the transseptal needle 80 or a proximal end of the transseptal needle 80 and associated damage to the sharp tip 29 of the transseptal guidewire 20.

Referring now to the drawings in detail, FIG. 1 illustrates the transseptal guidewire dispenser 100 assembled with the transseptal guidewire 20. Dispenser 100 is used to dispense the transseptal guidewire 20 so it may be advanced into the lumen (81, FIG. 6) of the transseptal needle (80, FIG. 6) for performing a surgical procedure. The guidewire 20 and transseptal needle 80 may be inserted into a sheath and then introduced through a patient's vein into the heart so the sharp tip 29 of the guidewire 20 may be used to puncture the intra-atrial septum.

Figure 2:
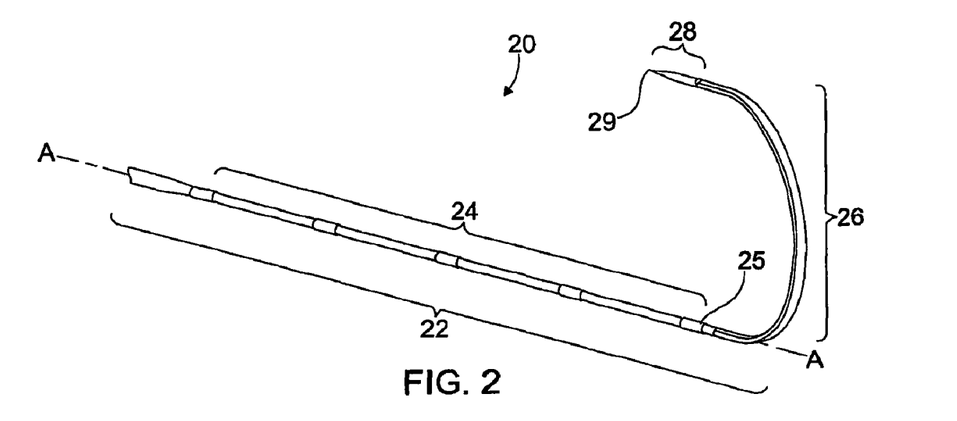
FIG. 2 is a perspective view of an embodiment of a transseptal guidewire of the transseptal guidewire dispenser assembly shown in FIG. 1.

As shown in FIG. 2, the transseptal guidewire 20 includes an elongated body 22, an end section 26, and a tapered distal section 28. The tapered distal section 28 terminates at the pointed tip 29 at the distal end of transseptal guidewire 20. In an exemplary embodiment, when transseptal guidewire 20 is positioned fully within a transseptal needle, transseptal guidewire 20 retains a substantially straight configuration. When end section 26 is not otherwise supported, it flexes to a curved conformation such as that shown for illustration purposes in FIG. 2. Thus, in use, when the distal end of the transseptal needle contacts the intra-atrial septum of a patient, transseptal guidewire 20 may extend so that pointed tip 29 perforates the intra-atrial septum and is positioned in the left atrium of the heart. As transseptal guidewire 20 continues along its path along axis A-A into the left atrium, end section 26 curves into a non-traumatic conformation so that the lateral wall of the left atrium is not exposed to pointed tip 29. Preferably, the tip 29 is sufficiently flexible so that it does not need the optional curve to be atraumatic.

A portion of end section 26 is ovalized such that end section 26 has a substantially non-circular cross section. Portion 24, however, has a substantially circular cross section relative to end section 26. In one embodiment, portion 24 is an imagable section having at least one radiopaque marker 25. Further details of transseptal guidewire 20 and methods for using transseptal guidewire 20 are described in U.S. patent application Ser. No. 11/875,365, which is incorporated herein in its entirety by reference.

Referring again to FIG. 1, dispenser 100 includes a holder 150 that has a lumen to contain the transseptal guidewire 20. Holder 150 is optionally provided in the form of a tube but may be any structure capable of holding or supporting at least a portion of the transseptal guidewire 20. According to an exemplary embodiment, holder 150 may have various diameters or sizes to accommodate guidewires 20 of different lengths and sizes. Guidewire 20 may be coiled within holder 150 to provide a compact dispenser 100. Holder 150 has a cross-sectional diameter that can accommodate guidewires 20 of different thicknesses so guidewire 20 may be slid in or out of the holder 150 as needed to advance or retract the guidewire 20 from holder 150.

According to an exemplary embodiment, holder 150 may be made out of a polymer or co-polymer such as high-density polyethene, low-density polyethylene, polyetherblockamide, nylon, polystyrene, or other suitable plastic material. The preferred material is high-density polyethylene. In other embodiments, holder 150 may be made out of any material that can be easily sterilized such as by the application of heat, chemicals, or irradiation prior to packaging or use before surgery. After surgery, it is contemplated that the entire dispenser 100 and guidewire 20 may be disposed, but the dispenser 100 and/or guidewire 20 can also be configured for sterilization and reuse.

Figure 6:
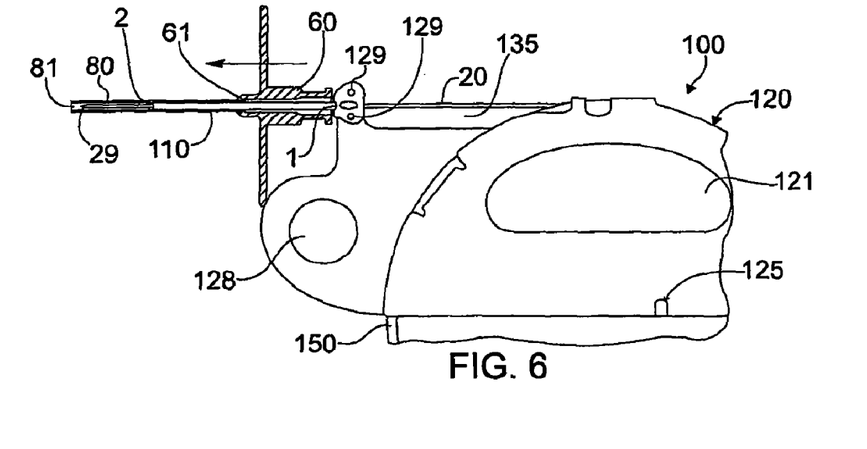
FIG. 6 is a plan view of an exemplary embodiment of a transseptal guidewire system including the transseptal guidewire dispenser assembly illustrated in FIG. 1 and a transseptal needle.
Figure 8A:
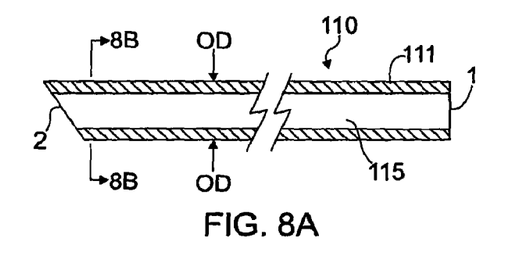
FIG. 8A is a cross-sectional side view of a shield component of the transseptal guidewire dispenser, the cross-section being taken along lines 8A-8A shown in FIG. 8B.
Figure 8B:
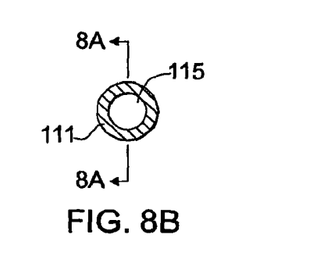
FIG. 8B is a cross-sectional end view of the shield component shown in FIG. 8A, the cross-section being taken along lines 8B-8B shown in FIG. 8A.

Referring now to FIGS. 1, 8A, and 8B, dispenser 100 also includes the shield 110 that is coupled to holder 150 by means of a handle component 120. In another embodiment, shield 110 may be directly coupled to holder 150. Shield 110 has a wall 111 defining a lumen 115 that is sized to accommodate transseptal guidewire 20. The cross-sectional shape of the wall 111 is constant or substantially constant along its length and sized to fit within the lumen 81 (FIG. 6) of the transseptal needle 80 (FIG. 6). An outer surface of the wall 111 of the shield 110 is cylindrical along its length between the proximal 1 and distal 2 ends of the shield 110 such that the outer diameter OD of wall 111 may be constant or substantially constant and sized to fit within the lumen 81 of the transseptal needle 80.

According to an exemplary embodiment, shield 110 may be flexible so it may be manipulated for insertion into the lumen 81 of the transseptal needle 80 or so that it may be bent in a packaged or stored configuration (FIG. 4) or partially bent (FIG. 5) to facilitate insertion into the hub and lumen of the needle. For example, the shield 110 may be made from a flexible rubber or polymer. Materials such as polyetherblockamide, polyurethane, polystyrene, high-density or low-density polyethylene, polyetherether ketone, polycarbonate, or nylon may be used though the preferred material is polycarbonate. It is contemplated that other polymeric or metallic or alternative materials for shield 110 may also be used.

As further illustrated in FIG. 1, a portion of transseptal guidewire 20 is inserted through the shield 110 such that a gap 135 (FIG. 4) exists between holder 150 and shield 110 to provide access to transseptal guidewire 20 for finger manipulation. Transseptal guidewire 20 has a J-shaped end portion near tip 29 that extends beyond shield 110. According to an exemplary embodiment, tip 29 is flexible so that when guidewire 20 is retracted into holder 150, the tip 29 may straighten in shield 110. This prevents the sharp tip 29 from contacting the hub 60 of the transseptal needle 80, shown in FIG. 6, as the sharp tip 29 is advanced into the lumen 115 of the shield 110, thereby minimizing or preventing damage to the tip 29. In another embodiment, sharp tip 29 is substantially straight such that when transseptal guidewire 20 is advanced or retracted from holder 150, the tip 29 does not contact the wall 111 of shield 110.

As shown in FIG. 1, dispenser 100 also includes a handle component 120. Handle component 120 is coupled to holder 150, but can be optionally excluded from dispenser 100 as well or formed integrally with holder 150. Handle component 120 includes a handle opening 121 and finger opening 128 so that dispenser 100 may be easily transported and held in placed during surgery. According to an exemplary embodiment, handle component 120 may be molded plastic or cut from a sheet of material and separately attached to dispenser 100. According to an exemplary embodiment, handle component 120 may be made out of a polymer or co-polymer such as high-density polyethene, low-density polyethylene, polyetherblockamide, nylon, polystyrene, polycarbonate, glycol-modified polyethylene terephthalate (PETG), or other suitable plastic material. The preferred material is PETG. Handle component 120 made also be made from other materials such as medical grade high density paper. It is contemplated that handle component 120 may be made from other materials as well. Additional aspects of the handle component 120 will be described in detail below.

Referring again to FIG. 2, aspects of the transseptal guidewire 20 are described in further detail. Transseptal guidewire 20 is configured to perforate the intra-atrial septum of the heart and is disposed within holder 150 so that transseptal guidewire 20 is reciprocally and axially moveable within holder 150. If necessary, the transseptal guidewire 20 can be rotated as well. Transseptal guidewire 20 has a length longer than transseptal needle (80, FIG. 6) and a diameter sized to fit through the lumen of commercially available transseptal needles.

As mentioned above, transseptal guidewire 20 includes an elongated body 22, an end section 26, and a tapered distal section 28. The tapered distal section 28 terminates at the pointed tip 29 at the distal end of transseptal guidewire 20. In an exemplary embodiment, when transseptal guidewire 20 is positioned fully within shield 110, transseptal guidewire 20 retains a substantially straight configuration. When transseptal guidewire 20 extends through the distal end of shield 150 along longitudinal axis A-A (FIG. 2), end section 26 is no longer supported within shield 150 and flexes to a curved conformation shown in FIG. 2.

As also illustrated in FIG. 2, elongated body 22 of transseptal guidewire 20 has a portion 24 proximal of end section 26. Portion 24 has a substantially circular cross section relative to end section 26. In an embodiment, portion 24 is an imagable section 24 having radiopaque markers 25 coupled to the imagable section 24. Radiopaque markers 25 may be made of a platinum/iridium alloy that emit low level radiation to the area surrounding imagable section 24 to assist with imaging of the operative area. In an exemplary embodiment, when a portion of imagable section 24 extends into the left atrium from the perforation hole (not shown), radioactive imaging of radiopaque markers 25 may confirm successful perforation of the intra-atrial septum. Radiopacity of markers 25 is generally equal or greater than transseptal needle 20, thus eliminating the need for radioscopy fluid solution.

Figure 3:
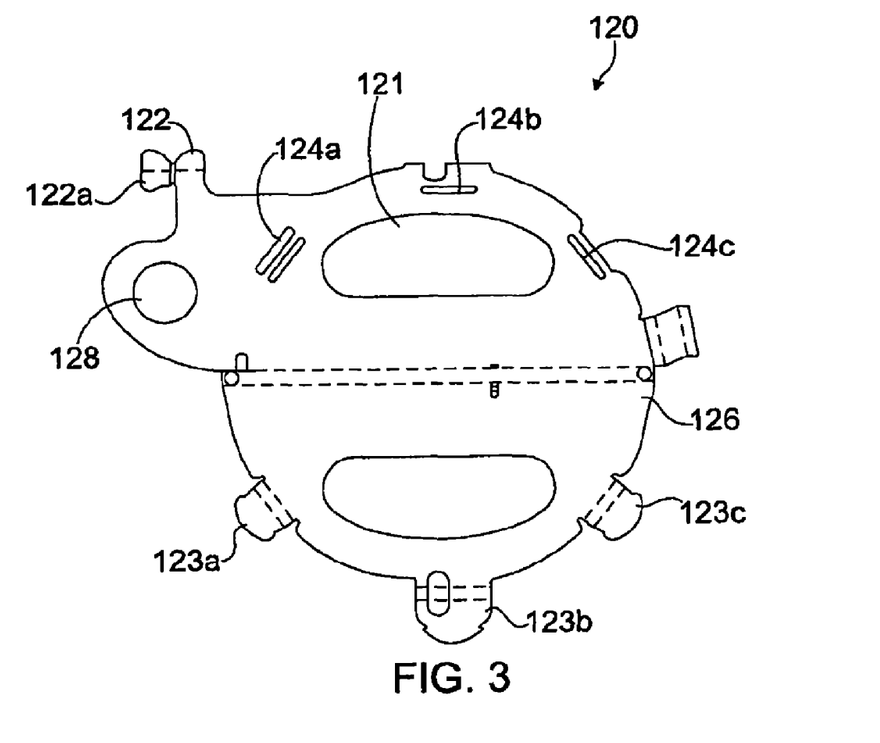
FIG. 3 is a plan view of an embodiment of a handle component of the transseptal guidewire dispenser assembly shown in FIG. 1, illustrated in an unfolded condition.
Figure 4:
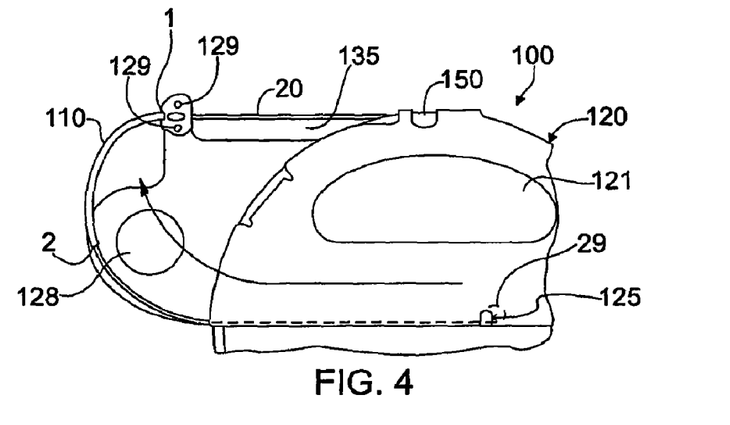
FIG. 4 is a plan view of a portion of the transseptal guidewire dispenser assembly shown in FIG. 1, illustrating an end portion of the transseptal guidewire in a stored position.
Figure 5:
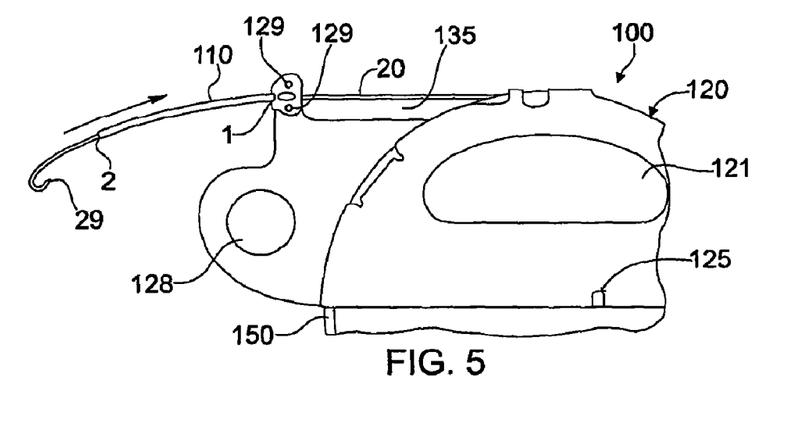
FIG. 5 is a plan view of a portion of the transseptal guidewire dispenser assembly shown in FIG. 1, illustrating an end portion of the transseptal guidewire being retracted into a holder component of the transseptal guidewire dispenser.

Referring now to FIG. 3, the handle component 120 of dispenser 100 is illustrated in an unfolded condition. Handle component 120 includes a wall 126 that may be folded over to provide a handle opening 121 for dispenser 100. Handle component 120 includes tabs 123a-c that also fold over and engage slots 124a-c to attach handle component 120 to holder 150. Handle component 120 also includes an extension 122 configured to support a portion of transseptal guidewire 20. A flap 122a adjacent extension 122 may be folded about the vertical fold line with respect to extension 122 to provide an aperture through which the shield 110 can be inserted and mounted. As shown in FIGS. 4-6, flap 122a may be bonded at 129 to extension 122 in at least one location to provide the aperture through which the shield 110 may be mounted. According to an exemplary embodiment, bonds 129 may be formed using conventional techniques such as heat bonding, ultrasonic bonding, gluing, or pressure bonding. Other bonding methods may also be used. Shield 110 is coupled to extension 122 to facilitate insertion of guidewire 20 into a lumen of transseptal needle (80, FIG. 6) while inhibiting damage to the sharp tip 29 of transseptal guidewire 20, as will be described in greater detail below.

Shield 110 is attached to extension 122 by adhesive, heat bond, ultrasonic bond, or other attachment means, depending on the materials of the shield 110 and the handle component 120. As described above, handle component 120 is optionally die cut from a sheet of material such as a polymeric material, vacuum formed, molded, or produced in other known manners. It is then folded in half about the holder 150 along the broken horizontal lines shown in FIG. 3. The tabs 123a-c are then folded over along the broken lines and inserted into the corresponding slots 124a-c to form the handle. The resulting handle component 120 has finger openings 128 so that the dispenser 100 can be grasped by the user during a surgical procedure.

Referring now to FIGS. 4-6, use of the dispenser 100 is illustrated. Specifically, FIGS. 4-6 illustrate a dispensing system in various positions, including a stored position in which the dispenser 100 with transseptal guidewire 20 can be packaged for sale, shipment, and storage (FIG. 4); a preparatory position in which the transseptal guidewire 20 is moved from the stored position toward a position in which the tip 29 will be shielded within the shield 110 (FIG. 5); and an extended position in which the tip 29 of transseptal guidewire 20 is extended from the distal end 2 of the shield 110 and advanced into the lumen 81 of the transseptal needle 80. Together, the dispenser 100, the transseptal guidewire 20, and the transseptal needle 80 form a dispenser system.

Referring specifically to FIG. 4, to inhibit damage, protect the sterile package, and retain the curvature of the J-shaped tip 29 of transseptal guidewire 20 during shelf-life, a distal portion of guidewire 20 is engaged onto a tab 125 of handle component 120 outside of the shield 110. When transseptal guidewire dispenser 100 is in use, guidewire 20 is first disengaged from tab 125 of handle component 120 and retracted into shield 110 in a direction indicated by the arrow shown in FIGS. 4 and 5.

Referring now to FIG. 6, when the pointed tip 29 of transseptal guidewire 20 is positioned within the lumen of shield 110, a portion of shield 110 is then inserted into a transseptal needle 80 such that the distal end surface 2 of shield 110 lies in a plane that is transverse to the lumen of transseptal needle 80 and distal of the hub 60 of the needle. In the illustrated cross-section of transseptal needle 80, hub 60 includes a tapered chamber through which the shield 110 may be inserted. The cross-sectional shape of the shield 110 is substantially constant and sized to fit within the lumen of transseptal needle 80. For example, the outer diameter of shield 110 may be smaller than the inner diameter of the transseptal needle lumen so it may fit inside transseptal needle 80. Thus, when guidewire 110 is positioned to extend into the lumen of transseptal needle 80 in a direction shown by the illustrated arrow in FIG. 6, contact is inhibited or prevented between the sharp tip 29 of transseptal guidewire 20 and hub 60.

Figure 7:
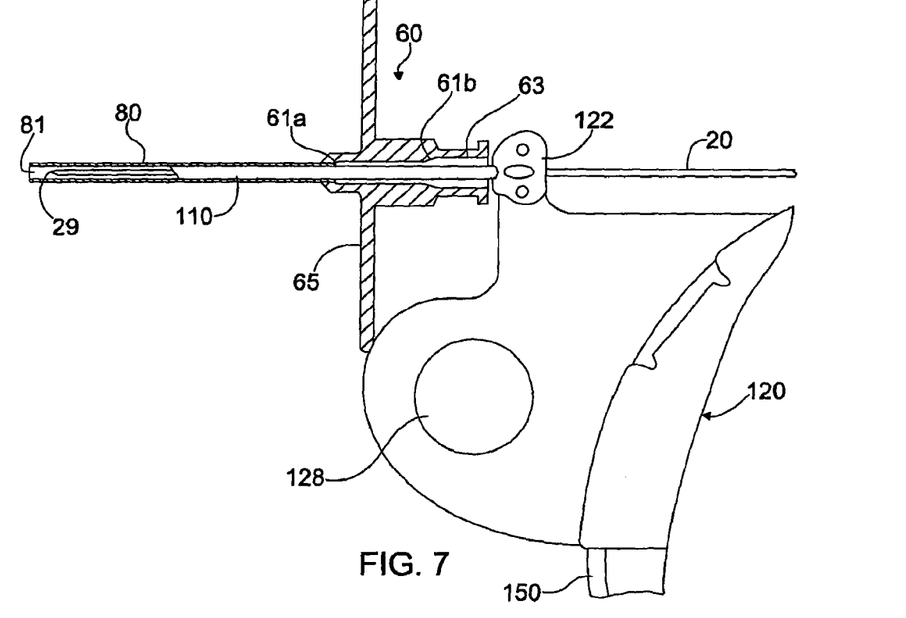
FIG. 7 is an enlarged plan view of the transseptal guidewire system shown in FIG. 6.

Referring now to FIG. 7, an enlarged view of the transseptal needle 80 and hub 60 is illustrated. Hub 60 optionally includes a flange 65 that may be positioned against a portion of handle component 120 to align shield 110 with a distal position within the lumen 81 of the transseptal needle 80. In other words, the handle component 120 may be provided with a surface, such as portion 122 of the handle component 120, to restrict the depth that shield 110 can be inserted into the needle hub 60. The handle may or may not come into contact with the flange 65 or have any surface positioned to contact the flange 65 of the hub 60. In this way, the depth to which the shield 110 can be advanced within the needle 80 can be limited. Because there is no or little resistance between the shield and the needle's lumen, and because there is no surface of shield 110 to limit its insertion into the needle's lumen, the optional contact between the handle component and the flange 65 of the hub 60 can provide such a limit.

According to an embodiment, when shield 110 is inserted within hub 60, an annular recess 63 exists between the outer surface of shield and the inner surface of the hub 60. Hub 60 has shoulder 61a, 61b that facilitates the insertion of shield 110 into a portion of the transseptal needle lumen 81. While shoulders 61a, 61b provide transitions between interior regions of the hub 60 and the proximal end of the constant cross-sectional lumen 81 of the needle, such shoulders 61a, 61b may bind the sharp tip 29 of the transseptal guidewire 20 (especially if the tip 29 is at the terminal end of a J tip).

According to an exemplary embodiment, when the distal tip 2 of shield 110 contacts shoulders 61a, 61b, the distal tip of shield 110 is guided past shoulder 61a, 61b and into the lumen 81 of transseptal needle 80. As the sharp tip 29 of transseptal guidewire 20 is advanced beyond the distal tip 2 of shield 110 and into the lumen 81 of the transseptal needle 80, damage to the sharp tip 29 of transseptal guidewire 20 is inhibited or prevented.

As further illustrated in FIG. 7, the end surface of shield 110, such as the distal tip 2, may be oriented at an acute angle with respect to a longitudinal axis of the shield 110. The angled distal tip 2 of shield 110 may facilitate advancement of the end surface of shield 110 into and through hub 60 when the tip 2 contacts shoulders 61a, 61b. Alternatively, the distal tip 2 of the shield 110 may lie in a plane that is perpendicular to the longitudinal axis. Accordingly, the distal tip 2 of shield 110 may be blunt, yet still able to be inserted into the transseptal needle lumen 81 when it contacts shoulder 61a, 61b.

Without shield 110, it is contemplated that proper insertion of a J-shaped transseptal guidewire 20 into the lumen of transseptal needle 80 would damage the sharp tip 29. Similarly, in an embodiment with a substantially straight guidewire 20, when the sharp tip 29 of guidewire 20 contacts shoulders 61a and/or 61b, it is contemplated that the sharp tip 29 may be damaged and thus, render the guidewire 20 unusable. It is also contemplated that the dispenser assembly 100 can be used with a needle that does not have a shoulder in a transition between a hub and a lumen. Even without such a shoulder, the shield of the dispenser facilitates introduction of the transseptal guidewire into the lumen of the needle.

Referring now to FIGS. 7, 8A, and 8B, additional aspects of shield 110 are illustrated. As described above, shield 110 has a wall 111 that is substantially cylindrical along its length so the shield 110 may be inserted through the hub 60 and into the lumen 81 of transseptal needle 80. Thus, the outer diameter of shield 110 is sized such that it fits within the lumen 81 of transseptal needle 80. For example, the outer diameter of shield 110 is smaller than the diameter of the transseptal needle lumen 81 for unrestricted advancement of the shield 110 into the transseptal needle lumen 81. The wall 111 of shield 110 defines a lumen 115 having a circular cross-sectional area along the length of shield 110 so it is sized to accommodate transseptal guidewire 20 and prevent damage to the sharp tip 29.

Although an exemplary embodiment of shield 110 in the form of a cylindrical tube is illustrated in FIGS. 8A and 8B, other embodiments are contemplated as well. For example, the outer surface of the wall 111 of the shield 110 may have a non-cylindrical shape, and the cross-sectional shape of the outer surface of the wall 111 may be non-circular. Also, the inner surface of the wall 111 of the shield 110 may have a non-cylindrical shape, and the cross-sectional shape of the inner surface of the wall 111 may be non-circular.

Although the present invention has been particularly described in conjunction with specific embodiments, it is evident that many alternatives, modifications, and variations will be apparent to those skilled in the art. It is therefore contemplated that the appended claims will embrace any such alternatives, modifications, and variations as falling within the true scope and spirit of the present invention.

What is claimed:

1. An apparatus for introducing a sharp tip of a transseptal guidewire, the apparatus comprising:
   a transseptal guidewire;
   a transseptal needle having a hub and a lumen;
   a holder configured to contain the transseptal guidewire; and a shield coupled to the holder, the shield having a wall defining a lumen sized to accommodate the sharp tip of the transseptal guidewire, the cross-sectional shape of the wall being constant along a length that is sized to fit within the lumen of the transseptal needle, thereby inhibiting contact between the sharp tip of the transseptal guidewire and the hub of the transseptal needle when the wall of the shield is positioned to extend into the lumen of the transseptal needle;

wherein the wall of the shield along at least the distal portion of its length has an outer diameter smaller than an inner diameter of the lumen of the transseptal needle;

wherein the lumen of the shield has a substantially constant cross-sectional area along at least a portion of its length between proximal and distal ends of the shield, thereby facilitating insertion of the sharp tip of the transseptal guidewire through the lumen of the shield; and wherein an outer surface of the wall of the shield is cylindrical along the length that is sized to fit within the lumen of the transseptal needle, thereby facilitating insertion of the shield into the lumen of the transseptal needle.

2. The apparatus of claim 1, further comprising a handle component coupled to the holder.

3. The apparatus of claim 2, wherein the shield is coupled to the handle.

4. The apparatus of claim 1, wherein the shield is indirectly coupled to the holder.

5. The apparatus of claim 1, the apparatus defining a gap between the holder and the shield, thereby providing access to the transseptal guidewire at said gap.

6. The apparatus of claim 1, wherein the shield is made of a polymer.

7. The apparatus of claim 6, the wall of the shield being flexible.

8. The apparatus of claim 1, wherein a proximal portion of the lumen of the transseptal needle has a constant diameter and the shield has a length sufficient to extend into said proximal portion of the lumen of the transseptal needle.

9. The apparatus of claim 1, wherein an end surface at the distal end of the shield is oriented at an angle acute with respect to a longitudinal axis of the shield, thus facilitating advancement of the distal end of the shield past a shoulder between the hub and the lumen of the transseptal needle.

10. The apparatus of claim 9, the end surface of the shield lying in a plane.

11. The apparatus of claim 1, said holder comprising a tube.

12. The apparatus of claim 1, wherein the shield is fixed to the holder.

13. The apparatus of claim 1, wherein the transseptal needle is provided with the holder in a kit.

14. The apparatus of claim 1, the transseptal guidewire having a curved tip.

15. The apparatus of claim 1, the transseptal needle having a sharp tip.

16. A system for perforating an intra-atrial septum comprising:

a transseptal needle having proximal and distal ends, a hub positioned at the proximal end, and a lumen extending from the hub to the distal end;

a transseptal guidewire having a sharp tip sized to extend through the lumen of the transseptal needle;

a holder at least partially containing the transseptal guidewire; and a shield coupled to the holder, the shield having a wall defining a lumen sized to accommodate the sharp tip of the transseptal guidewire, wherein an outer surface of the wall of the shield is cylindrical along a length that is sized to fit within the lumen of the transseptal needle, thereby facilitating insertion of the shield into the lumen of the transseptal needle;

the transseptal guidewire having a retracted position in which the sharp tip of the transseptal guidewire is contained within the lumen of the shield and an extended position in which the sharp tip of the transseptal guidewire extends distally from the shield and into the lumen of the transseptal needle;

the shield having a first position in which the distal end of the shield does not extend into the lumen of the transseptal needle and a second position in which the distal end of the shield extends into the lumen of the transseptal needle to a position that is distal of the hub of the transseptal needle;

wherein a proximal portion of the lumen of the transseptal needle has a constant diameter and the shield has a length sufficient to extend into said proximal portion of the lumen of the transseptal needle; and wherein the transseptal guidewire is in the retracted position when the shield is in the first position and the transseptal guidewire is moved to the extended position when the shield is in the second position, thereby inhibiting contact between the sharp tip of the transseptal guidewire and the hub of the transseptal needle or the proximal end of the transseptal needle when the shield is in the second position.

17. The system of claim 16, further comprising a handle component coupled to the holder.

18. The system of claim 17, wherein the shield is coupled to the handle.

19. The system of claim 16, wherein the shield is indirectly coupled to the holder.

20. The system of claim 16, the assembly defining a gap between the holder and the shield, thereby providing access to the transseptal guidewire.

21. The system of claim 16, wherein the shield is made of a polymer.

22. The system of claim 16, wherein the shield is tubular.

23. The system of claim 22, wherein an outer surface of the wall of the shield is cylindrical along its length between the proximal and distal ends of the shield.

24. The system of claim 16, wherein an end surface of the shield is oriented at an angle acute with respect to a longitudinal axis of the shield, thus facilitating advancement of the end surface of the shield past a shoulder between the hub and the lumen of the transseptal needle.

25. The system of claim 24, the end surface of the shield lying in a plane.

26. The system of claim 16, the transseptal guidewire having a curved tip.

* * * * *